United States Patent
Turcott

[11] Patent Number: 5,712,801
[45] Date of Patent: Jan. 27, 1998

[54] METHOD FOR CHARACTERIZING DYNAMICAL SYSTEMS

[75] Inventor: Robert Turcott, Redwood City, Calif.

[73] Assignee: Pacesetter, Inc., Sunnyvale, Calif.

[21] Appl. No.: 533,292

[22] Filed: Sep. 25, 1995

[51] Int. Cl.$^6$ ............................................. A61B 5/02
[52] U.S. Cl. ...................... 364/550; 395/924; 128/661.04
[58] Field of Search ........................ 364/413.02, 413.05, 364/551.01, 550, 578; 395/924; 128/661.04, 700, 705

[56] References Cited

U.S. PATENT DOCUMENTS

| | | | |
|---|---|---|---|
| 4,732,157 | 3/1988 | Kaplan et al. | 128/696 |
| 4,893,632 | 1/1990 | Arnington | 128/696 |
| 5,148,812 | 9/1992 | Verrier et al. | 128/704 |
| 5,201,321 | 4/1993 | Fulton | 128/702 |
| 5,404,880 | 4/1995 | Throne | 128/705 |
| 5,439,004 | 8/1995 | Duong-van et al. | 128/705 |
| 5,447,519 | 9/1995 | Peterson | 607/5 |
| 5,453,940 | 9/1995 | Broomhead et al. | 364/553 |
| 5,562,596 | 10/1996 | Pincus et al. | 600/17 |

OTHER PUBLICATIONS

"Is Fibrillation Chaos?", Kaplan, et al., Circulation Research, vol. 67, No. 4, Oct. 1990, pp. 886–892.

"Lack of Evidence for Low–Dimensional Chaos in Heart Rate Variability", Kanters, et al., Nonlinear Dynamics in Heart Rate, pp. 591–601.

Primary Examiner—Emanuel T. Voeltz
Assistant Examiner—Thomas Peeso
Attorney, Agent, or Firm—Steven M. Mitchell

[57] ABSTRACT

A method for characterizing the degree of similarity between phase space representations of trajectories of different dynamical systems. This method provides a computationally efficient technique for comparing different dynamical systems, or different dynamics exhibited by the same system. A first trajectory is designated as a template against which other trajectories are compared. A test trajectory is characterized by providing a measure based on determining the smallest distance between each point of the test trajectory to the template and then determining the largest of these smallest distances. The similarity of the two trajectories is quantified by establishing a lattice or grid for the phase space. For each lattice point, the distance, as given by a metric defined for the space, is calculated to the nearest point of the template trajectory. The minimum distance is retained and associated in a memory for each lattice point. The test trajectory is generated in the phase space with each data point of the test trajectory landing in a bin having a lattice point at its center. The previously determined shortest distance of that lattice point to the template trajectory is fetched from memory to provide an approximation of the closest distance of each point in the test trajectory to the template trajectory. The maximum of these distances among all points in the test trajectory serves as the distance between the two trajectories, and hence as a measure of degree of similarity between the two trajectories.

18 Claims, 5 Drawing Sheets

SIMPLE OSCILLATOR

DAMPED OSCILLATOR

METHOD FOR CHARACTERIZING DYNAMICAL SYSTEMS

FIELD OF THE INVENTION

The present invention relates generally to a method for comparing different dynamical systems or different dynamics exhibited by the same system, and more particularly to a method for discriminating among different dynamics of a patient's heart.

BACKGROUND OF THE INVENTION

A dynamical system is a system that can be described by a set of coupled differential equations. The degrees of freedom, m, of the system is the number of variables needed to characterize the system's behavior, or equivalently, the number of equations in the set of coupled, first-order differential equations that define the system. A phase space is a mathematical m-dimensional space where each dimension is associated with one of the m system variables. Since the state of the system at a particular time is given by the value of each variable, the state can be represented by the location of a point in the phase space. As the system evolves with time, the value of each variable changes, and the point characterizing the state of the system moves in the space. The time-evolution of the system is thus characterized by the trajectory of the point in phase space. The trajectory is determined by the differential equations governing the system, so the phase space representation embodies the dynamical properties of the equations.

These concepts are illustrated in FIGS. 1a–c and 2a–c. A simple oscillator has two degrees of freedom: the position and velocity. The dependence of these variables on time is shown in FIGS. 1a and 1b. Plotted against each other in phase space, as shown in FIG. 1c, these variables execute an ellipse. The state of the system moves along the ellipse as the position and velocity oscillate. The ellipse characterizes the dynamics of an oscillator.

When friction is added to the dynamics, the amplitude of the variables decay with time, as shown FIGS. 2a and 2b for a damped oscillator. The decreasing amplitude causes the trajectory in phase space to spiral to the origin as illustrated in FIG. 2c. The very different behavior of the two systems is thus readily apparent in the phase space representations shown in FIGS. 1c and 2c.

In analyzing experimental data, one typically has access to a single variable, such as position, rather than the entire set of m state variables. One of the profound insights that has arisen from chaos theory is the recognition that a topologically equivalent representation of phase space can be constructed from the observation of a single variable. Access to all the state variables is therefore unnecessary.

The ability of tiered-therapy implantable cardioverter defibrillators (ICDs) to deliver appropriate therapy depends in part on their ability to discriminate among various cardiac arrhythmias. The primary parameter used for discrimination has been heart rate. Other characteristics of electrograms which have been used are suddenness of onset of a high rate, rate stability, and morphology of the QRS complex. The limited computational capacity of contemporary devices has, for morphology-based discriminators, led developers to focus on techniques that rely on rather superficial properties of the electrogram. It is desirable to develop an algorithm which operates on the fundamental properties of the electrogram, but is not computationally intensive.

An arrhythmia of ventricular origin is conducted throughout the ventricles by a different path than the specialized conduction system which conveys supraventricular rhythms. As used herein, supraventricular rhythms include both normal rhythms such as sinus rhythm as well as arrhythmias of supraventricular origin such as atrial fibrillation. The different pathways used by ventricular and supraventricular rhythms have different dynamics, which give rise to differences in morphology between these two classes of rhythms. It would be beneficial to have an arrhythmia discrimination algorithm which treats electrograms as having arisen from a dynamical system.

It is reasonable to view the voltage recorded by an electrogram as arising from a dynamical system. Different systems are responsible for propagation through the myocardium and the specialized conducting system. Differences between the trajectories of rhythms of ventricular and supraventricular origin should then be apparent in the reconstructed phase space. An algorithm based on this approach is thus more than just an empirical technique: it relies on the differences in the fundamental dynamics of the system, the same information given by the differential equations that model the system. However, since our interest is in discrimination, and not in identifying the intrinsic properties of the putative dynamical systems, the necessary degree of rigor is greatly relaxed. For example, it is not necessary to determine the true dimensionality of the system or address issues of noise; it is sufficient to simply extract enough of the dynamical differences that the systems can be distinguished.

It is therefore an object of the present invention to provide a method for distinguishing between different dynamical systems, or different dynamics exhibited by the same system.

It is a further object of the invention to provide a computationally efficient method for representing and comparing phase space trajectories.

SUMMARY OF THE INVENTION

The present invention provides a computationally efficient technique for comparing different dynamical systems. This technique can also be used to compare different dynamics arising from the same system. The invention may be applied particularly in the detection and discrimination of cardiac arrhythmias as manifest by ventricular electrogram morphology. A mathematical representation of the dynamics of a waveform is obtained from a single measurable variable, particularly electrogram signal amplitude in the preferred embodiment, by using the technique of delay embedding. This representation, which is a trajectory in an abstract space, is topologically equivalent to the attractor that describes the system dynamics, and hence reflects fundamental properties of the rhythm.

In a preferred embodiment, a first phase space representation or trajectory is generated for use as a template from, for example, a first cardiac rhythm electrogram of known origin. A second or test trajectory is generated from a second cardiac rhythm electrogram for a detected waveform complex. This second trajectory is compared to the template to distinguish between different dynamics and thus the origins of the first and second cardiac rhythms. If a test trajectory is sufficiently different from the template trajectory, the test complex is deemed to have different dynamics, and therefore be from a different rhythm than the template. For example, ventricular tachycardia can be distinguished from conducted supraventricular rhythms when this formulation is applied to electrograms recorded locally in the ventricle with a normal sinus rhythm serving as the template.

In the preferred embodiment, comparison of the trajectories is accomplished by determining the distance in phase space of each point of the test trajectory to the closest point on the template trajectory. The largest of these shortest distances is used to characterize the similarity of the test trajectory to the template trajectory. The distance between two trajectories is determined in the following way. A lattice or grid is established for the phase space during template formation. For each point in the lattice, the distance, as given by a metric decreed for the space, is calculated to each point of the template trajectory. The minimum distance is retained and associated in a memory with the lattice point. When the algorithm is run, each point of the trajectory of the test electrogram specifies a lattice point in the phase space. The distance associated with the lattice point is fetched from memory to provide an approximation of the shortest distance to the template trajectory. The maximum of these distances among all points in the test trajectory serves as the distance between the two trajectories, and hence as a measure of degree of similarity between the dynamics of the two rhythms.

In the preferred embodiment, the metric, or distance measure, used is the square of the Euclidean norm, $$d(\bar{x},\bar{y}) = \sum_{i=1}^{m} (x_i - y_i)^2,$$

where $x_i$ and $y_i$ are the $i^{th}$ components of the vectors $\bar{x}$ and $\bar{y}$, and m is the dimensionality of the space. Other metrics are possible, such as the $1^\infty$ norm (read "1-infinity"), $$d(\bar{x},\bar{y}) = \max_i |x_i - y_i|,$$

or the $1^1$ norm, $$d(\bar{x},\bar{y}) = \sum_{i=1}^{m} |x_i - y_i|.$$

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE PREFERRED EMBODIMENT

The invention will first be considered with a discussion of the representation of a dynamical system in phase space. A trajectory in an m-dimensional phase space is reconstructed from a sequence of samples $\{x_i\}$ by forming a sequence of vectors $\{\bar{x}_j\}=\{[x_j, x_{j-l}, \ldots, x_{j-(m-1)l}]\}$, where l is the lag. For example, with m=3 and l=2, and with the sequence of samples being $\{x_i\}$, the sequence of vectors would be $[x_5, x_3, x_1]$, $[x_6, x_4, x_2]$, $[x_7, x_5, x_3]$, . . . . In this example, the sequence of vectors would trace out a trajectory in three dimensional space. This simple technique of delay embedding generates a trajectory that is topologically equivalent to that of the true phase space.

As the dimension of phase space used to represent the system increases, the computational demands of the method of the invention increase exponentially. In addition, there is an upper limit to the dimensionality of the space, beyond which no further improvement in discrimination is expected. It has been found that for distinguishing cardiac rhythms a three dimensional space is preferred.

The optimal lag l for delay embedding depends on the details of the data. If l is short relative to the time scale over which the electrogram fluctuates, then the components of the vector will be similar in magnitude, and a trajectory will be executed that falls close to the diagonal. If l is long then the first component of the vector will have returned to zero by the time the second component encounters a QRS complex and begins to climb away from zero. The trajectory will then consist largely of excursions along the axes. The optimal lag is one which spreads the trajectory out in phase space. Theoretical considerations suggest that the first zero crossing $\tau_0$ of the autocorrelation function provides a good lag time. This lag time is 9 msec for the preferred embodiment.

Figure 1A:
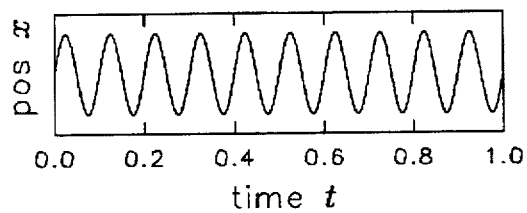
FIGS. 1a–c illustrate the phase space representation of a simple oscillator.
Figure 2A:
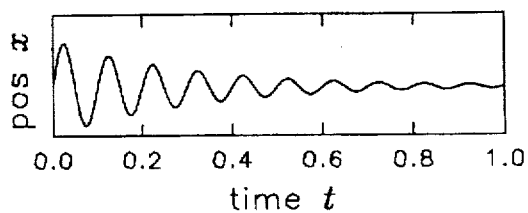
FIGS. 2a–c illustrate the phase space representation of a damped oscillator.
Figure 1B:
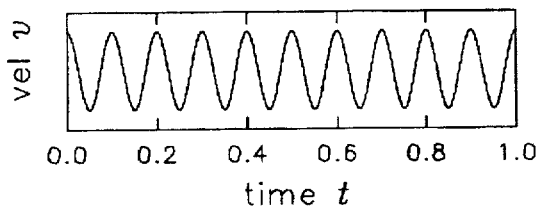
Figure 2B:
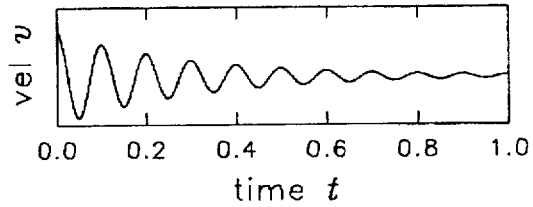
Figure 1C:
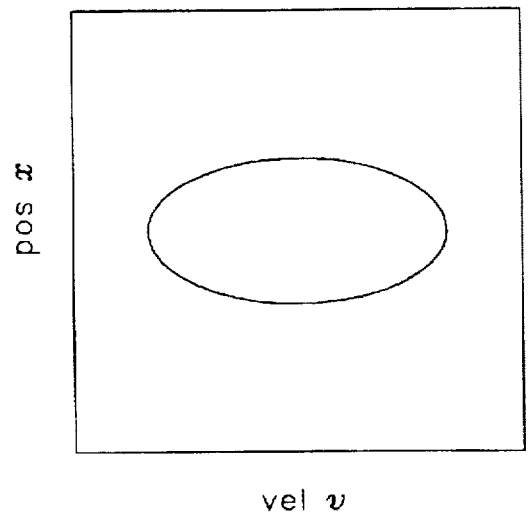
Figure 2C:
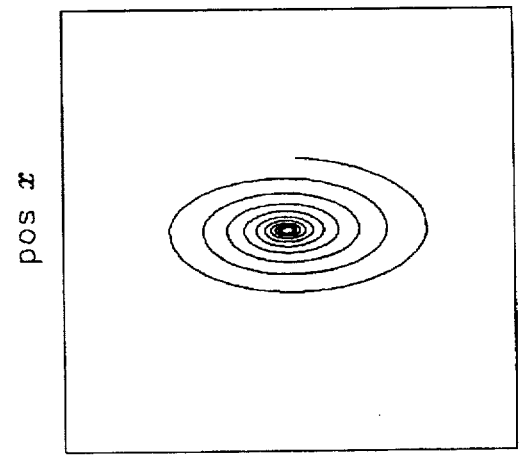
Figure 3:
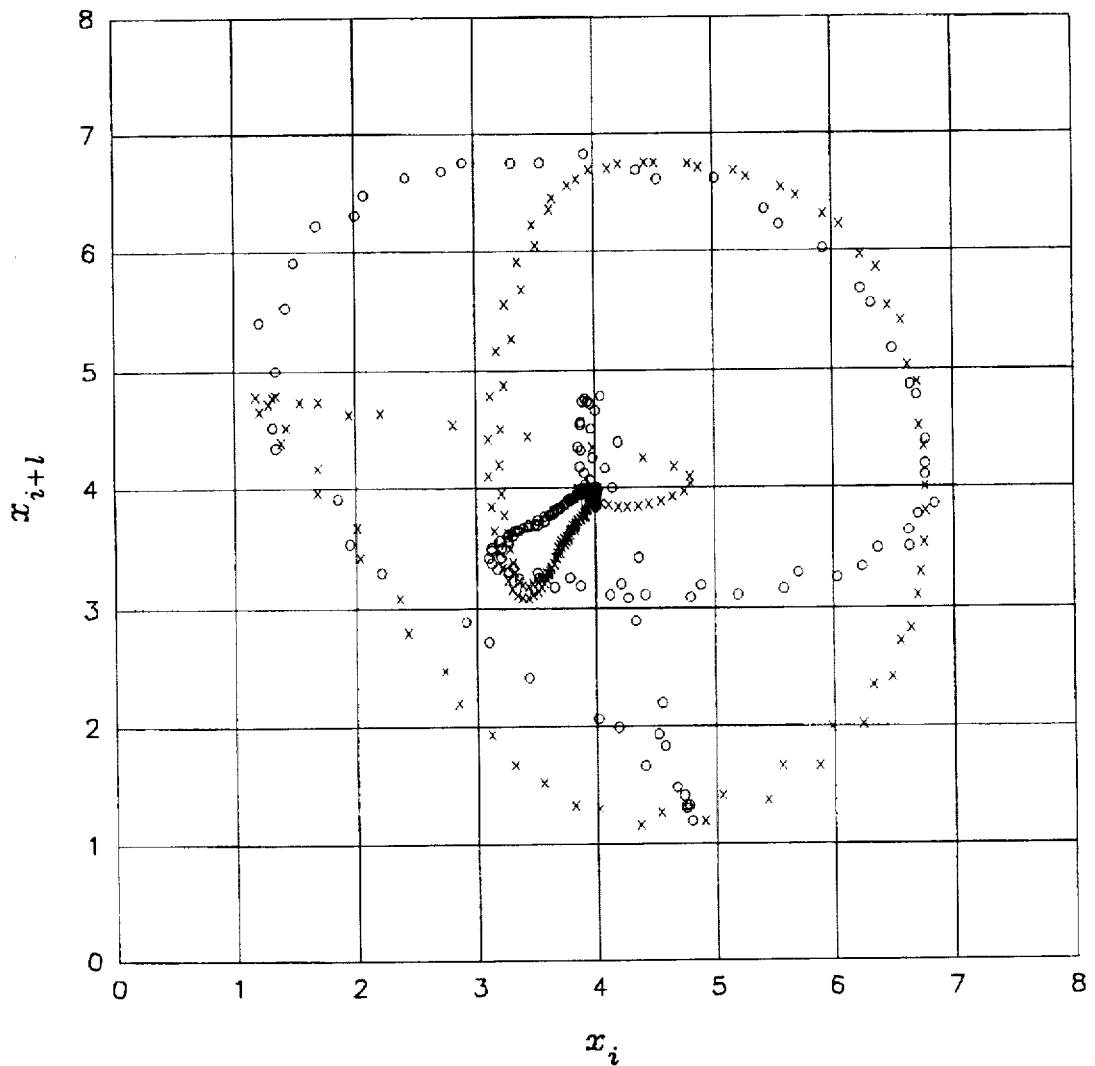
FIG. 3 is a two dimensional plot of the trajectories of two different cardiac rhythms in phase space.

Referring now to FIG. 3, the steps for providing an error measure that reflects the degree of similarity between two trajectories in m-dimensional space will be discussed. The value of the error measure can be used to infer the origin of the cardiac rhythm. This will be discussed in more detail below with reference to FIGS. 4 and 5. A template trajectory is constructed, preferably from an electrogram of a sinus rhythm for a given patient. The trajectories are sets of vectors, represented graphically as sets of points distributed in space. FIG. 3 illustrates a plot for m=2 dimensions. A higher dimension provides better separation between the trajectories and, as mentioned above, m=3 is used in the preferred embodiment. However, m=2 is used here for convenience of illustration. An 8×8 grid is established, creating 64 bins with the centers of the bins providing a lattice of points which are used for the distance calculations. In the figure the symbols 'X' and '0' represent trajectories from different rhythms. It should be understood that no physical plot or display is required or desired to practice the invention in an ICD. In practice, constructing or creating a trajectory involves storing numbers in a memory.

The template is constructed by first obtaining the set of vectors generated by the template rhythm which is preferably of supraventricular origin, typically a sinus rhythm. One or more QRS complex may be used to generate the template. Because the trajectories do not have time as a variable, the starting point of the trajectory construction is not relevant. The space is partitioned into bins, and the distance from the center of each bin to each point of the template trajectory is calculated. The minimum distance between the center of each bin and the template trajectory is recorded and associated with the bin in memory. Since the dynamics of a given patient's cardiac system may change over time, it may be desirable to replace the template from time to time with a new template, again preferably based on a sinus rhythm.

When the discrimination algorithm is run, a trajectory is executed for each test QRS complex. Each vector in the trajectory will fall in a bin. The minimum distance to the template trajectory, which was calculated for each bin during template generation, is fetched from memory for each vector. The largest of these distances approximates the largest distance from the test trajectory to the template and is returned as the error measure of the test complex relative to the template. This technique requires substantially less computational complexity than would be required to calculate the distance between every point in a test complex and every point in the template. The distance from the center of the bin to the template trajectory is an approximation of the distance from the test vector to the template trajectory. The error in the approximation can be made arbitrarily small by increasing the resolution of the spatial quantization. However, this increases computational complexity and may not be necessary to achieve the desired discrimination capability. It has been found that sufficient resolution is obtained with an 8×8×8 grid having 512 bins.

If the error measure is sufficiently large, the test complex is deemed to be different from the template rhythm. For example, if a supraventricular rhythm were used in generating the template (e.g., atrial fibrillation or sinus rhythm), then a large error measure would indicate that the test rhythm is of ventricular origin, (e.g., ventricular tachycardia), and appropriate therapy would be delivered.

A great advantage of this algorithm for low-powered devices is that no calculations need to be performed after the template has been formed. The error measure of each complex is obtained by memory accesses and compares.

In order to further reduce the computational requirements of the system of the invention, the discrimination algorithm may be triggered to run only when there is a need to determine whether a rhythm is of ventricular or supraventricular origin. The algorithm may be triggered each time the detected heart rate exceeds a predetermined threshold and/or at such time as other discriminating criteria provide a trigger.

Computational savings are achieved during template formation by effectively neglecting trajectory points near the origin. Since the electrogram voltage is near zero during diastole, bins near the origin of the phase space will contain the vast majority of points, yet these points contain no information about the dynamics of the waveform. For this reason, points near the origin are excluded from the error calculation. Thus, in the preferred embodiment, no calculations are performed for template trajectory points falling in the 8 bins around the phase space origin. Rather, the distances associated with these lattice points are automatically set to zero.

Figure 4:
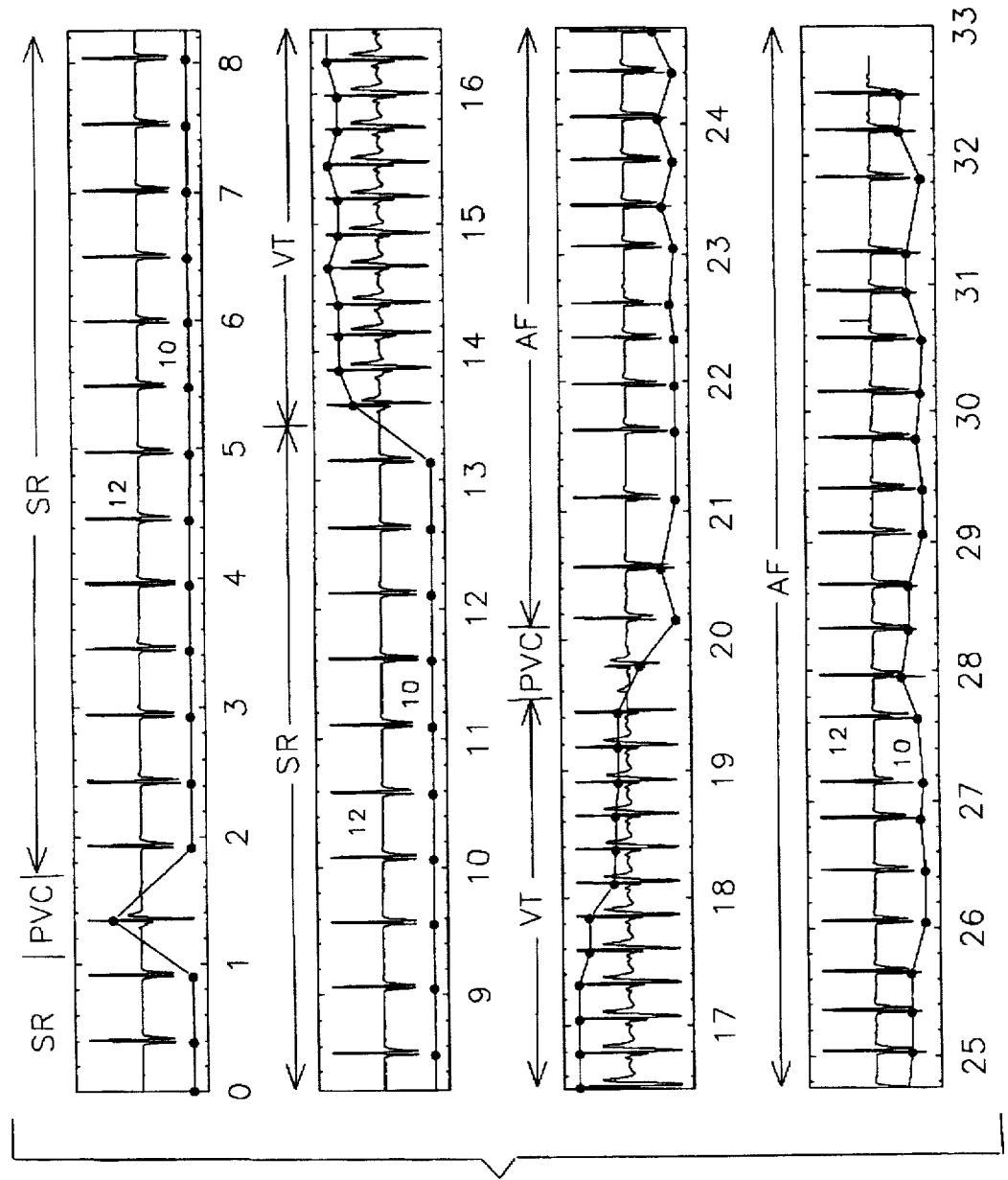
FIG. 4 gives the output of the arrhythmia discrimination algorithm for each QRS complex in a stored electrogram.

FIG. 4 presents an example of the output 10 of the discrimination algorithm generated from a stored electrogram 12. The electrogram 12 is annotated above each panel, where SR is sinus rhythm, PVC is premature ventricular contraction, VT is ventricular tachycardia, and AF is atrial fibrillation. These results were obtained using m=3, l=9 msec, and a test-trajectory resolution of N=8 bins per dimension. A Euclidean metric, defined above, was used for distance calculations. The 10 sinus complexes between t=1.8 sec and t=6.6 sec served as the template. For purposes of this example, the complexes used to generate the template are also compared against the template. As expected, the results of these comparisons are close to zero.

Figure 5:
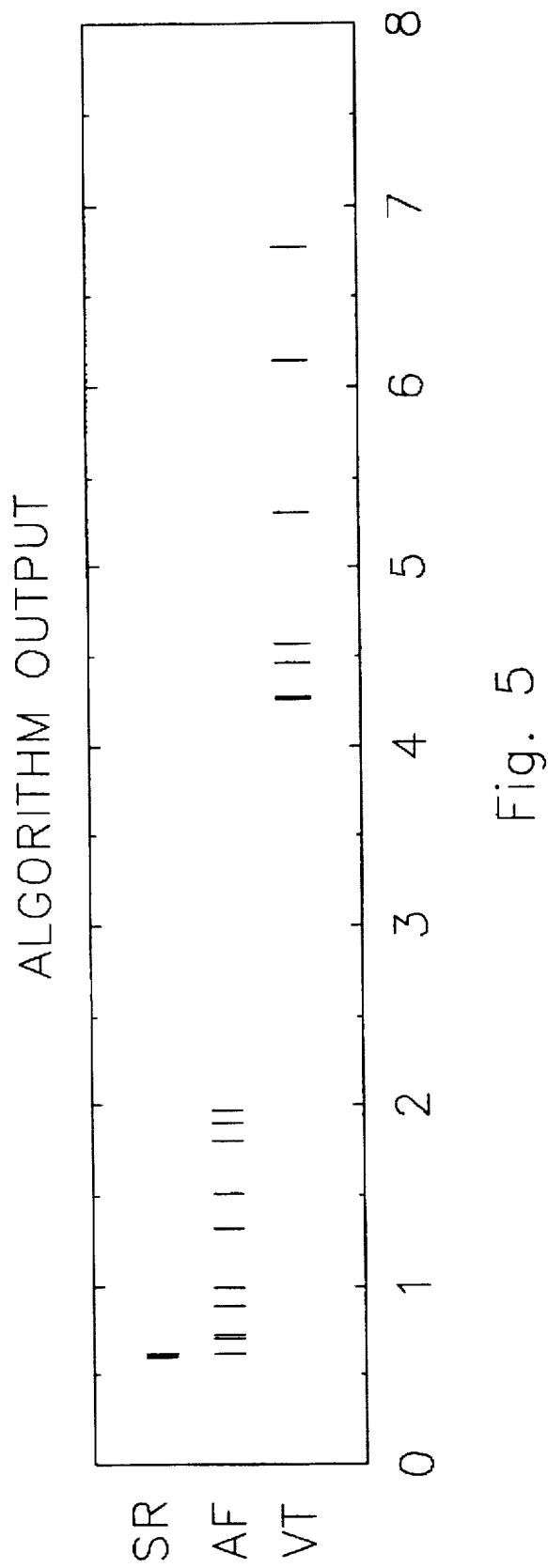
FIG. 5 gives the output of the arrhythmia discrimination algorithm grouped by cardiac rhythm.

The error measure or qualifier output, grouped according to rhythm, is presented in FIG. 5. As shown in this figure, a range of thresholds (2.0≦θ≦4.2) would successfully distinguish ventricular tachycardia from the supraventricular rhythms.

Figure 6:
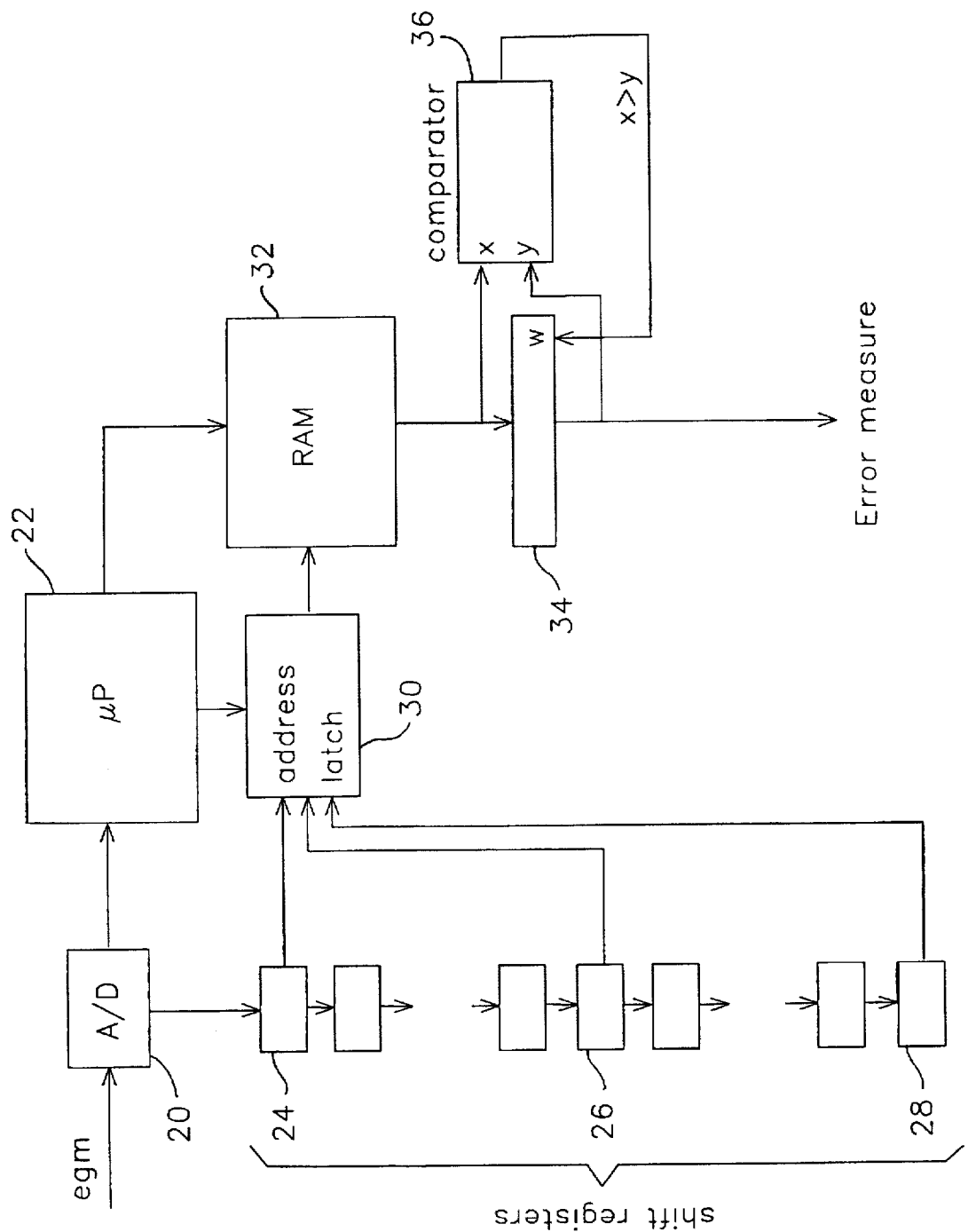
FIG. 6 is a schematic diagram of a hardware implementation of the invention.

The invention may be practiced by implementation in hardware or software or some combination of the two. A hardware implementation of a preferred embodiment of the invention will now be discussed with reference to FIG. 6. An electrogram signal is received from a bipolar ventricular sensor (not shown) by an analog to digital converter 20. The analog to digital converter 20 provides a first output to a microprocessor and related hardware 22 for heart rate analysis and other desired processing. The sampling period is preferably 1 msec but other rates can be used. A second output from analog to digital converter 20 is provided to a string of 19 3-bit shift registers. Since the space is quantized to 8 bins per dimension, the 3 most significant bits of each sample are sufficient to uniquely specify one component of the bin's address. A first shift register 24, a tenth shift register 26 and a last (nineteenth) shift register 28 together provide the address containing the distance associated with the corresponding lattice point. The address is latched in an address latch 30 and presented to a random access memory (RAM) 32 which contains the shortest distance from each of the 512 bins to the template trajectory. When a memory location in RAM 32 is accessed, it provides an output to output register 34. This output from RAM 32 is also provided to a comparator 36. Comparator 36 determines whether the output from RAM 32 is greater than the value currently stored in register 34. If the new value is larger, the output of comparator 36 enables the write function of register 34 to write the new value from RAM 32 over the old value in register 34. In this way, the largest of the minimum distances from the test trajectory to the template trajectory is determined. The output is the error measure for each QRS complex which may be used by microprocessor 22 to determine the appropriate therapy. In addition, these error measures may be recorded in memory linked to a stored electrogram to assist a physician in later diagnosis.

The invention has been described with reference to a preferred embodiment of an implantable defibrillator which senses a ventricular intracardiac electrogram. However, other dynamical systems such as other biological or physical systems could be analyzed using the invention.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. A method for characterizing a degree of similarity between phase space representations of trajectories arising from different dynamical systems comprising the steps of:
   designating a first one of said trajectories as a template against which others of said trajectories are to be compared;
   determining a measure of a shortest distance in phase space of each point of a second trajectory to said template trajectory; and
   determining the largest of said shortest distances to provide a characterizing value.

2. The method of claim 1 wherein said step of determining a measure of a shortest distance comprises computing a square of a Euclidean norm in phase space.

3. The method of claim 1 further comprising the steps of:
   obtaining a set of points in phase space generated by said template;
   partitioning said phase space into a grid of bins;
   determining a measure of a shortest distance of each bin to a closest point of said template and storing such measure for each bin in a memory; and
   determining for each point of said phase space representation of said second trajectory the bin into which it falls and fetching from said memory the measure of said shortest distance for said bin;

wherein said step of determining a measure of a shortest distance includes to determining which of said bins each point of said second trajectory falls into and fetching from said memory the measure of said shortest distance for said bin.

4. The method of claim 3 and further including the step of setting to zero said measure for those points of said template trajectory which represent the least relevant system information.

5. The method of claim 1 wherein said phase space representations are generated by plotting a trajectory in an m-dimensional phase space from a sequence of samples $\{x_i\}$ provided as amplitude data points of an electrogram by forming a sequence of vectors $\{\bar{x}_j\}=\{[x_j, x_{j-l}, \ldots, x_{j-(m-1)l}]\}$, where l is a lag time.

6. A method for characterizing a degree of similarity between phase space representations of trajectories of different dynamical systems comprising the steps of:

designating a first trajectory as a template against which other trajectories are compared;

establishing a lattice for the phase space;

determining a measure of a distance from each lattice point to a closest point of said template trajectories and storing said measure in a memory;

determining a closest lattice point for each data point of a second trajectory and fetching said distance measure from said lattice point from said memory; and determining a largest of said measures fetched from said memory to characterize said test trajectory.

7. The method of claim 6 wherein said step of determining a closest lattice point includes generating an m-dimensional bin around each of said lattice points and determining which of said bins each of said second trajectory data points falls into.

8. The method of claim 6 wherein said step of determining a measure of a distance from each lattice point includes the step of setting to zero said measure for those points of said template trajectory which represent the least relevant system information.

9. A system for characterizing a degree of similarity between phase space representations of trajectories arising from different dynamical systems comprising:

means for designating a first one of said trajectories as a template against which others of said trajectories are to be compared;

means for determining a measure of a shortest distance in phase space of each point of a second trajectory to said template trajectory; and means for determining the largest of said shortest distances to provide a characterizing value.

10. A method for characterizing a degree of similarity between phase space representations of trajectories arising from different dynamics of a dynamical system comprising the steps of:

designating a first one of said trajectories as a template against which others of said trajectories are to be compared;

determining a measure of a shortest distance in phase space of each point of a second trajectory to said template trajectory; and determining the largest of said shortest distances to provide a characterizing value.

11. The method of claim 10 wherein said step of determining a measure of a shortest distance comprises computing a square of a Euclidean norm in phase space.

12. The method of claim 10 further comprising the steps of:

obtaining a set of points in phase space generated by said template;

partitioning said phase space into a grid of bins;

determining a measure of a shortest distance of each bin to a closest point of said template and storing such measure for each bin in a memory; and determining for each point of said phase space representation of said second trajectory the bin into which it falls and fetching from said memory the measure of said shortest distance for said bin;

wherein said step of determining a measure of a shortest distance includes determining which of said bins each point of said second trajectory falls into and fetching from said memory the measure of said shortest distance for said bin.

13. The method of claim 12 and further including the step of setting to zero said measure for those points of said template trajectory which represent the least relevant system information.

14. The method of claim 10 wherein said phase space representations are generated by plotting a trajectory in an m-dimensional phase space from a sequence of samples $\{x_i\}$ provided as amplitude data points of an electrogram by forming a sequence vectors $\{\bar{x}_j\}=\{[x_j, x_{j-l}, \ldots, x_{j-(m-1)l}]\}$, where l is a lag time.

15. A method for characterizing a degree of similarity between phase space representations of trajectories of different dynamics of a dynamical system comprising the steps of:

designating a first trajectory as a template against which other trajectories are compared;

establishing a lattice for the phase space;

determining a measure of a distance from each lattice point to a closest point of said template trajectory and storing said measure in a memory;

determining a closest lattice point for each data point of a second trajectory and fetching said distance measure from said lattice point from said memory; and determining a largest of said measures fetched from said memory to characterize said test trajectory.

16. The method of claim 15 wherein said step of determining a closest lattice point includes generating an m-dimensional bin around each of said lattice points and determining which of said bins each of said second trajectory data points falls into.

17. The method of claim 15 wherein said step of determining a measure of a distance from each lattice point includes the step of setting to zero said measure for those points of said template trajectory which represent the least relevant system information.

18. A system for characterizing a degree of similarity between phase space representations of different trajectories of a given dynamical system comprising:

means for designating a first one of said trajectories as a template against which others of said trajectories are to be compared;

means for determining a measure of a shortest distance in phase space of each point of a second trajectory to said template trajectory; and means for determining the largest of said shortest distances to provide a characterizing value.

* * * * *